United States Patent [19]

Mark et al.

[11] 4,304,899

[45] Dec. 8, 1981

[54] POLYCARBONATE COMPOSITIONS HAVING IMPROVED BARRIER PROPERTIES

[75] Inventors: Victor Mark, Evansville; Charles V. Hedges, Mt. Vernon, both of Ind.

[73] Assignee: General Electric Company, Mt. Vernon, Ind.

[21] Appl. No.: 112,703

[22] Filed: Jan. 16, 1980

Related U.S. Application Data

[63] Continuation-in-part of Ser. No. 929,255, Jul. 31, 1978, abandoned.

[51] Int. Cl.³ .......................................... C08G 63/62
[52] U.S. Cl. .................................. 528/171; 528/196; 528/204
[58] Field of Search ............... 528/171, 196, 219, 204; 568/722, 723, 727, 728; 260/463

[56] References Cited

U.S. PATENT DOCUMENTS

| | | | |
|---|---|---|---|
| 2,936,272 | 5/1960 | Bender et al. | 568/727 |
| 3,028,365 | 4/1962 | Schnell | 260/47 |
| 3,169,121 | 2/1965 | Goldberg | 260/47 |
| 3,367,980 | 2/1968 | Zaweski | 568/727 |
| 3,398,120 | 8/1968 | Hindersinn et al. | 528/182 |
| 3,422,065 | 1/1969 | Wulff et al. | 528/171 |

OTHER PUBLICATIONS

Chem. Abstracts, vol. 64, No. 4, 2/1966 (6832d).

*Primary Examiner*—Theodore E. Pertilla
*Attorney, Agent, or Firm*—Martin B. Barancik; William F. Mufatti

[57] ABSTRACT

Polycarbonate compositions having improved barrier properties; i.e., low water vapor transmission and low gas permeability, are obtained by employing selected mono- and di-alkyl substituted monomers.

9 Claims, 1 Drawing Figure

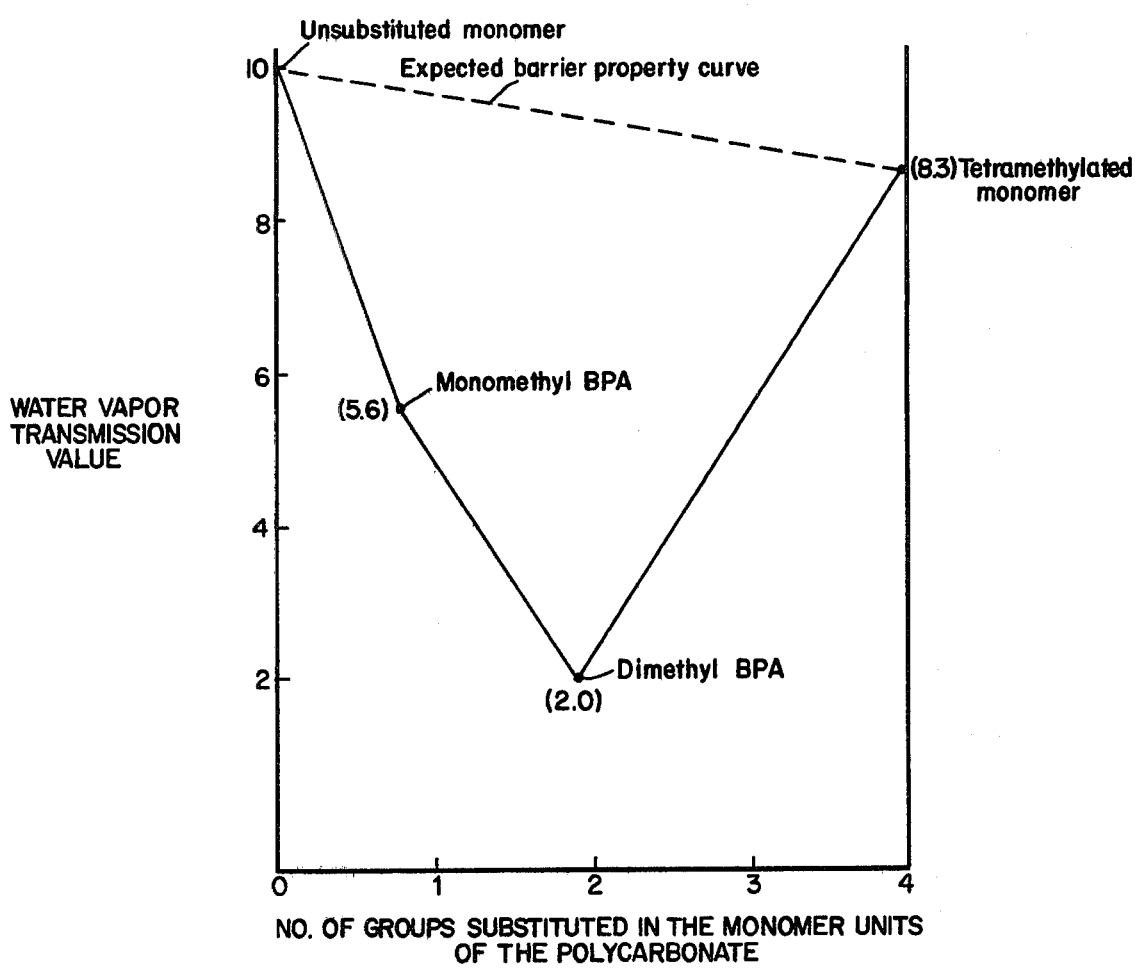

POLYCARBONATE COMPOSITIONS HAVING IMPROVED BARRIER PROPERTIES

This application is a continuation-in-part application of copending application Ser. No. 929,255 filed July 31, 1978 now abandoned.

This invention relates to high molecular weight aromatic polycarbonate compositions having improved barrier properties; i.e., low water vapor transmission and low gas permeability.

BACKGROUND OF THE INVENTION

Polycarbonate polymers are known as being excellent molding materials since products made therefrom exhibit such properties as high impact strength, toughness, high transparency, wide temperature limits (high impact resistance below $-60°$ C. and a UL thermal endurance rating of $115°$ C. with impact), good dimensional stability, good creep resistance, and the like.

Dimethylated aromatic polycarbonates are known as disclosed in U.S. Pat. No. 3,028,365. Tetramethylated aromatic polycarbonates are also known and their high heat distortion properties have been recognized as disclosed in U.S. Pat. No. 3,879,384. It would be desirable to add to this list of properties those of low water vapor transmission and low gas permeability to enable the aromatic polycarbonates to be used to form containers and film wraps for foods, beverages, cosmetics, and the like. In particular, food and beverage containers made from aromatic polycarbonates having these added barrier properties would be more economical as they would be capable of reuse and would thus also help reduce the impact of environmental waste occasioned by broken glass and discarded, non-reuseable containers.

SUMMARY OF THE INVENTION

It has now been found that mono- and di-alkyl substituted, high molecular weight aromatic polycarbonates can be obtained that exhibit improved water vapor transmission and gas barrier properties, as compared to non-alkylated aromatic polycarbonates.

It has been further surprisingly found that mono- and dialkylated aromatic polycarbonates exhibit far superior barrier properties than either non-alkylated or tetramethylated aromatic polycarbonates.

The alkylated aromatic polycarbonates of this invention can be prepared by known techniques using appropriate monomers such as are disclosed in copending applications Ser. No. 882,242, filed Feb. 28, 1978; Ser. No. 882,191, filed Feb. 28, 1978; and Ser. No. 882,192, filed Feb. 28, 1978 which are assigned to the same assignee as this case and which are incorporated herein by reference.

The monomers that can be employed are bisphenols which contain at least one unsubstituted alkyl moiety bonded directly to one of the phenyl groups, are halogen-free, and do not include cyclic and/or aryl groups bonded directly to a phenyl group. These monomers can be represented by the following general formula:

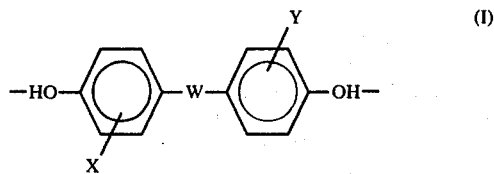
(I)

wherein the X and Y moieties can each independently be selected from the group consisting of hydrogen, an unsubstituted alkyl of $C_1$–$C_{10}$, and mixtures thereof with the proviso that at least either X or Y is a $C_1$–$C_{10}$ alkyl; and, W is a member selected from the following group:

(a) $-(CH_2)_r-$ wherein r is 0 or an integer from 2–10;

(b)

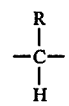

wherein R is a member selected from the group consisting of $C_1$–$C_{10}$ alkyl, $C_5$–$C_{10}$ cycloalkyl and $C_6$–$C_{14}$ aryl;

(c)

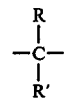

wherein R and R' can each independently be the same as R in (b) above with the proviso that, when both R and R' are each $CH_3$, X and Y are not both symmetrically substituting $CH_3$;

(d)

wherein m is an integer of 4–20;

(e)

wherein p and q can each independently be an integer of 0–1; and, (f) $-O-$.

Typical of some of the monomers that can be employed in this invention are bis(4-hydroxy-3-methylphenyl)methane, 1,6-bis(4-hydroxy-3-ethylphenyl)hexane, 2,2-(4-hydroxyphenyl)(4-hydroxy-3-methylphenyl)propane, 1,1-bis(4-hydroxy-3-methylphenyl)propane, 1,1-bis(4-hydroxy-3-methylphenyl)cyclohexane, bis(4-hydroxy-3-ethylphenyl)sulfone, bis(4-hydroxy-3-isopropylphenyl)ether and the like.

Of course, it is possible to employ two or more different monomers of a copolymer with a glycol or with hydroxy or acid terminated polyester, or with a dibasic acid in the event a carbonate copolymer or interpolymer rather than a homopolymer is desired for use in preparing the aromatic polycarbonate. Blends of any of these materials can also be used to obtain the aromatic polycarbonates.

These high molecular weight aromatic polycarbonates can be linear or branched homopolymers or copolymers as well as mixtures thereof or polymeric blends and generally have an intrinsic viscosity (IV) of about 0.40–1.0 dl/g as measured in methylene chloride at 25° C. These high molecular weight aromatic polycarbonates can be typically prepared by reacting a monomer with a carbonate precursor.

The carbonate precursor used can be either a carbonyl halide, a carbonate ester or a haloformate. The carbonyl halides can be carbonyl bromide, carbonyl chloride and mixtures thereof. The carbonate esters can be diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc., di-(alkylphenyl) carbonates such as di(tolyl) carbonate, etc., di-(naphthyl) carbonate, di-(chloronaphthyl) carbonate, phenyl tolyl carbonate, chlorophenyl chloronaphthyl carbonate, etc., or mixtures thereof. The haloformates that can be used include bis-haloformates of dihydric phenols (bis-chloroformates of hydroquinone, etc.) or glycols (bishaloformates of ethylene glycol, neopentyl glycol, polyethylene glycol, etc.) as well as haloformates of the monomers described above in formula I. While other carbonate precursors will occur to those skilled in the art, carbonyl chloride, also known as phosgene, is preferred.

Also included are the polymeric derivatives of a dihydric phenol, a dicarboxylic acid and carbonic acid such as are disclosed in U.S. Pat. No. 3,169,121 which is incorporated herein by reference.

Molecular weight regulators, acid acceptors and catalysts can also be used in obtaining the aromatic polycarbonates of this invention. The useful molecular weight regulators include monohydric phenols such as phenol, chroman-I, paratertiarybutylphenol, primary and secondary amines, etc. Preferably, phenol is employed as the molecular weight regulator.

A suitable acid acceptor can be either an organic or an inorganic acid acceptor. A suitable organic acid acceptor is a tertiary amine such as pyridine, triethylamine, dimethylaniline, tributylamine, etc. The inorganic acid acceptor can be either a hydroxide, a carbonate, a bicarbonate, or a phosphate of an alkali or alkaline earth metal.

The catalysts which can be employed are those that typically aid the polymerization of the monomers with phosgene. Suitable catalysts include tertiary amines such as triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethylammonium chloride, tetramethyl ammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

Also included herein are branched polycarbonates wherein a polyfunctional aromatic compound is reacted with the monomer and carbonate precursor to provide a thermoplastic randomly branched polycarbonate. These polyfunctional aromatic compounds contain at least three functional groups which are carboxyl, carboxylic anhydride, haloformyl, or mixtures thereof. Illustrative polyfunctional aromatic compounds which can be employed include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride and trimellitic acid or their acid halide derivatives.

Accordingly, the mono- and di-alkylated, high molecular weight aromatic polycarbonates of the invention can be represented by the following general formula:

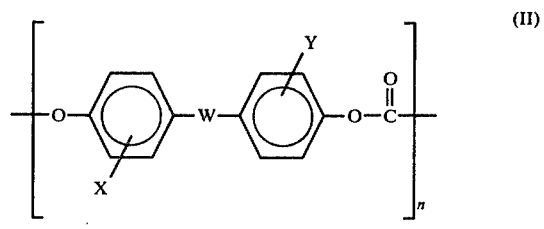

wherein X, Y and W are the same as in formula I above and n is an integer of about 2–2,000.

BRIEF DESCRIPTION OF THE FIGURE

The FIGURE shows water vapor transmission values dependent on the number of groups substituted in the monomer units of the polycarbonate.

PREFERRED EMBODIMENT OF THE INVENTION

The following examples are set forth to more fully and clearly illustrate the present invention and are intended to be, and should be construed as being, exemplary and not limitative of the invention. Unless otherwise stated, all parts and percentages are by weight.

The barrier properties for each of the ensuing examples were determined using Modern Controls, Inc. instruments. Water vapor transmission rate (WVTR) measurements were obtained on an IRD-2C instrument pursuant to ASTM F-372-73; carbon dioxide data ($CO_2TR$) were obtained using a Permatran-C instrument; and, oxygen transmission rates ($O_2TR$) were determined using an OX-TRAN 100 instrument. The methods used to obtain WVTR and $CO_2TR$ data are based on infrared analysis whereas the $O_2TR$ measurements are based on a coulometric method. The WVRT measurements are expressed in grams/24 hrs./100 in.$^2$/mil at 100° F. and 90% relative humidity (RH) whereas those of $CO_2TR$ and $O_2TR$ are expressed in cc/24 hrs./100 in.$^2$/mil/atmosphere.

EXAMPLE 1

Preparation of 4,4'-cyclohexylidenedi-o-cresol (CDC)

To a 22 l. three-necked flask, equipped with stirrer, subsurface gas inlet tube, thermometer and reflux condenser was charged 2180 g (22.2 moles) of cyclohexanone and 12000 g (111 moles) of o-cresol and to the resulting solution was introduced subsurface HCl gas with good stirring. A mildly exothermic reaction ensued; by external cooling, the temperature was not allowed to exceed 55°–60° C. The introduction of HCl was continued until blow-through was observed, when it was stopped. The progress of the reaction was followed by ir (infrared spectroscopy), which indicated that in ca. 1.5–2 hrs. all of the cyclohexanone was consumed, by the disappearance of the carbonyl band at 1710 cm$^{-1}$. Crystals started to come out of the warm solution in an additional 1–2 hours, which was facilitated and completed by cooling and stirring.

After the separation of crystals was complete, the reaction mixture was filtered and the filter cake was rinsed on the funnel with methylene chloride. The crystals were then slurried up in methylene chloride, filtered and the cake rinsed again. The crude crystals weighed 4285 g on 76.8% of theory. The cresolic mother liquor typically contained 270 g of the p,p'-product, whereas the methylene chloride mother liquors contained an additional 119 g of product, bringing the total conversion of the p,p'-isomer to 83%.

Recrystallization of the 4285 g of crude filtercake, which had an assay of 98.5% and a mp of 184–7° C., by dissolution in 9.5 l. of refluxing methanol and subsequent addition of 2.8 l. of water, followed by cooling, deposited colorless crystals that, after filtration and airdrying, weighed 3515 g (82% of the crude), and had an assay of 99.8–99.9%, mp 188–189° C.

EXAMPLE 2

Into a mixture of 74.1 parts of pure 4,4'-cyclohexylidenedi-o-cresol (CDC) (mp 188–189° C.; 0.25 parts mole), 300 parts water, 300 parts methylene chloride, 0.47 parts phenol and 0.5 parts triethylamine were introduced, at ambient temperature, 30 parts phosgene over a period of 30 minutes while maintaining the pH of the two-phase system at about 11; i.e., pH 10–12.5, by simultaneously adding a 25% aqueous sodium hydroxide solution. At the end of the addition period, the pH of the aqueous phase was 11.7 and the CDC content of this phase was less than 1 part per million (ppm) as determined by ultraviolet analysis.

The methylene chloride phase was separated from the aqueous phase, washed with an excess of dilute (0.01 N) aqueous HCl and then washed three times with deionized water. The polymer was precipitated by adding the neutral and salt-free methylene chloride solutions to an excess of methanol and filtering off the white polymer which was dried at 95° C. The resultant, pure CDC-polycarbonate had an intrinsic viscosity (IV) in methylene chloride at 25° C. of 0.554 dl/g. Its barrier properties are set forth in the Table.

EXAMPLE 3

The procedure of Example 2 was repeated, except that 4,4'-isopropylidenediphenol, (BPA), was substituted, in equivalent amounts, for CDC. The pure BPA-polycarbonate had an IV of 0.560 dl/g. Its barrier properties are listed in the Table.

EXAMPLE 4

The procedure of Example 2 was repeated, except that an equivalent amount of a 75 weight % CDC/25 weight % BPA mixture was used in place of only CDC. A copolycarbonate was obtained having an IV of 0.55 dl/g and that yielded colorless, transparent moldings or film. Its barrier properties are listed in the Table.

EXAMPLE 5

The procedure of Example 2 was repeated, except that an equivalent amount of a 55 weight % CDC/45 weight % BPA mixture was used in place of CDC. The resultant copolycarbonate, which yielded tough, transparent test objects and films, had an IV of 0.54 dl/g. Its barrier properties are listed in the Table.

EXAMPLE 6

Preparation of 4,4'-cyclohexylidenediphenol (CDP)

The procedure of Example 1 was repeated, except that 10500 g (111.6 moles) of phenol was substituted for o-cresol. The crude crystals that separated out were rinsed with methylene chloride; after airdrying they weighed 5170 g or 87% of theoretical. Recrystallization from methanol-water yielded pure CDP, mp 188–189° C., that was 99.8% pure by gas chromatography.

EXAMPLE 7

Preparation of 4,4'-(1-methylethylidene)bis-o-cresol (MEC)

The procedure of Example 1 was repeated except that 645 g (11.1 moles) of acetone was substituted for the cyclohexanone and heat was applied during the introduction of HCl to maintain the reaction temperature between 50°–70° C. The progress of the reaction was conveniently monitored by gas chromatography, which indicated that most of the 2,2'- and 2,4'-isomers formed at the beginning of the reaction rearranged to the 4,4'-isomer. When the concentration of this latter in the product had increased from an initial 63% to 93% (with only 7% of the 2,4'-isomer and no detectable amount of the 2,2'-isomer being present), the hydrochloric acid catalyst and the excess of o-cresol were removed by heating and distillation under water aspirator vacuum. The distillation residue, after recrystallization from chlorobenzene, yielded 2333 g (9.1 mole) or 82% of MEC, mp 135–7° C., that was 98.5% pure by gas chromatography.

EXAMPLE 8

Preparation of 4,4'-(1-methylpropylidene)bis-o-cresol (MPC)

The procedure of Example 6 was exactly repeated, except that 800 g (11.1 moles) of 2-butanone was substituted for acetone and the reaction temperature was kept at or below 50° C. Purification was effected by extracting the solid distillation residue twice with methylene chloride, which left behind the 4,4'-isomer as white crystals, mp 144°–146° C., 99.1% purity and 1840 g or 61.3% yield. This monomer, MPC, is believed to be novel.

EXAMPLE 9

Preparation of 4,4'-1-ethylpropylidene)bis-o-cresol (EPC)

The procedure of Example 6 was exactly repeated, except that 956 g (11.1 moles) of 3-pentanone was substituted for acetone. EPC was obtained in 99.2% purity, after recrystallization from cyclohexane, with a melting point of 119°–120° C. This monomer, EPC, is believed to be novel.

EXAMPLE 10

Preparation of 2-methyl-4,4'-(1-methylethylidene)bisphenol (MMEP)

Anhydrous HCl was introduced, with adequate cooling, into a mixture of 134 g (1.0 mole) of freshly prepared 4-isopropenylphenol (made by thermally cracking BPA in the presence of catalytic amounts of sodium hydroxide and separating it from the coproduct phenol by fractional vacuum distillation) and 540 g (5.0 moles) of o-cresol, while maintaining the temperature of the ensuing exothermic reaction below 50° C. After 4 hours, the red colored reaction mixture was stripped of HCl and excess cresol under water aspirator vacuum and the resultant straw colored melt was purified by recrystallization from cyclohexane. The 98.7% pure MMEP had a mp of 112°–113° C.

EXAMPLES 11–13

The preparation of polycarbonates by the procedure of Example 2 was repeated by substituting equivalent amounts of the following diphenols for CDC:

Example 11: MEC (4,4'-(1-methylethylidene)bis-o-cresol)

Example 12: MPC (4,4'-(1-methylpropylidene)bis-o-cresol)

Example 13: EPC (4,4'-(1-ethylpropylidene)bis-o-cresol)

The barrier properties of the resultant polycarbonates are listed in the Table.

EXAMPLES 14–18

The preparation of copolycarbonates with BPA by the procedure of Example 5 was repeated by substituting equivalent amounts of the following diphenols for CDC:

Example 14: CDP (4,4'-cyclohexylidenediphenol)

Example 15: MEC (4,4'-(1-methylethylidene)bis-o-cresol)

Example 16: MPC (4,4'-(1-methylpropylidene)bis-o-cresol)

Example 17: EPC (4,4'-1-ethylpropylidene)bis-o-cresol)

Example 18: MMEP (2-methyl-4,4'-(1-methylethylidene bisphenol)

The barrier properties of the resultant copolycarbonates are listed in the Table wherein Example 3, the BPA-polycarbonate, is used as the comparative standard.

Some of the test specimens from which the barrier properties were obtained were made by extruding the polycarbonates and copolycarbonates in an extruder operated at about 265° C. and, comminuting the extrudate into pellets. Thereafter, the pellets were compression molded into films having an average thickness of 10 mils. Other test specimens were obtained by film casting the polycarbonates and copolycarbonates directly from a methylene chloride solution to provide film specimens also having an average thickness of about 10 mils.

TABLE

Barrier Properties of Polycarbonates and Copolycarbonates

| Example | IV, dl/g | WVTR | CO$_2$TR | O$_2$TR |
|---|---|---|---|---|
| 2 | 0.554 | 0.7 | 20.4 | 10.2 |
| 3 | 0.560 | 10.0 | 875 | 200 |
| 4 | 0.550 | 1.6 | 148 | 34 |
| 5 | 0.540 | 2.7 | — | 56 |
| 11 | 0.548 | 2.7 | — | 33 |
| 12 | 0.526 | 2.0 | — | 34 |
| 13 | 0.555 | 1.4 | — | 28 |
| 14 | 0.547 | 6.2 | — | 110 |
| 15 | 0.542 | 4.8 | — | 122 |
| 16 | 0.552 | 5.5 | — | 140 |
| 17 | 0.538 | 5.2 | — | 132 |
| 18 | 0.544 | 5.6 | — | — |

The findings set forth in the foregoing examples and listed in the Table above are summarized in the FIGURE wherein the WVTR value of 8.3 was obtained from a polycarbonate produced from a tetramethylated bisphenol-A monomer following the procedure of Example 3 of U.S. Pat. No. 3,879,348 earlier identified and referred to.

As the FIGURE dramatically illustrates, the mono- and di- substituted polycarbonates have surprisingly far superior barrier properties than one would expect from either the unsubstituted or tetrasubstituted polycarbonates. Similar dramatic improvement in gas barrier properties were also obtained with mono- and di- substituted polycarbonates as compared with unsubstituted or tetrasubstituted polycarbonates as can be seen from the results listed in the Table.

What is claimed is:

1. A halogen-free high molecular weight aromatic polycarbonate compound having an IV of about 0.40–1.0 dl/g in methylene chloride at 25° C. and exhibiting improved water vapor transmission and gas barrier properties, said polycarbonate compound consisting essentially of the following general repeating unit:

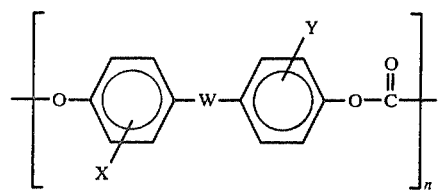

wherein the X and Y moieties can each independently be selected from the group consisting of hydrogen, an unsubstituted alkyl of C$_1$–C$_{10}$, and mixtures thereof with the proviso that at least either X or Y is a C$_1$–C$_{10}$ alkyl and that neither a cyclic nor an aryl group is bonded directly to a phenyl group; n is an integer of about 2–2,000; and, W is a member selected from the following group:

(a) $-(CH_2)_r-$ wherein r is 0 or an integer from 2–10;

(b)

wherein R is a member selected from the group consisting of C$_1$–C$_{10}$ alkyl, C$_5$–C$_{10}$ cycloalkyl and C$_6$–C$_{14}$ aryl;

(c)

wherein R and R' can each independently be the same as R in (b) above with the proviso that when both R and R' are each CH$_3$, X and Y are not both symmetrically substituting CH$_3$;

(d)

wherein m is an integer of 4–20;

(e)

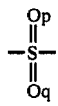

wherein p and q can each be an integer of 0–1; and, (f) —O—.

2. The polycarbonate compound of claim 1 wherein X and Y are each an unsubstituted $C_1$–$C_{10}$ alkyl.

3. The polycarbonate compound of claim 1 wherein X is an unsubstituted $C_1$–$C_{10}$ alkyl and Y is hydrogen.

4. The polycarbonate compound of claim 1 wherein the monomeric building block is 4,4'-cyclohexylidenedi-o-cresol.

5. The polycarbonate compound of claim 1 wherein the monomeric building block is 4,4'-cyclohexylidenediphenol.

6. The polycarbonate compound of claim 1 wherein the monomeric building block is 4,4'-(1-methylpropylidene)bis-o-cresol.

7. The polycarbonate compound of claim 1 wherein the monomeric building block is 4,4'-(1-ethylpropylidene)bis-o-cresol.

8. The polycarbonate compound of claim 1 wherein the monomeric building block is 2-methyl-4,4'-(1-methylethylidene)bisphenol.

9. A halogen-free high molecular weight copolymer having an IV of about 0.40–1.0 dl/g in methylene chloride at 25° C. and exhibiting improved water vapor transmission and gas barrier properties, said copolymer consisting essentially of the following general repeating units

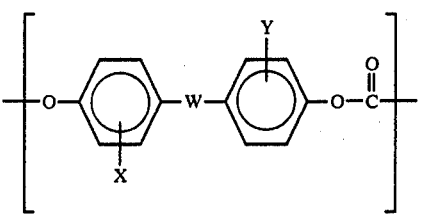

a.

wherein XY and W are defined as in Claim 1 and a second repeating unit

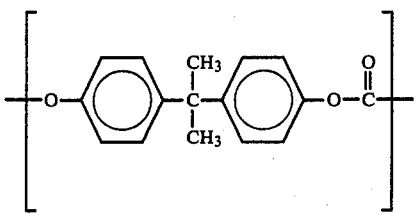

b.

* * * * *